United States Patent
Gebauer et al.

(10) Patent No.: US 9,943,781 B2
(45) Date of Patent: Apr. 17, 2018

(54) PARALLEL ASSEMBLY OF CHROMATOGRAPHY COLUMN MODULES

(75) Inventors: Klaus Gebauer, Uppsala (SE); Manoj Kumar Ramakrishna, Bangalore (IN); Daniel Salomonsson, Uppsala (SE); Per Uselius, Uppsala (SE)

(73) Assignee: GE HEALTHCARE BIOPROCESS R&D AB, Uppsala (SE)

( * ) Notice: Subject to any disclaimer, the term of this patent is extended or adjusted under 35 U.S.C. 154(b) by 384 days.

(21) Appl. No.: 13/701,251

(22) PCT Filed: Jun. 1, 2011

(86) PCT No.: PCT/SE2011/050681
§ 371 (c)(1),
(2), (4) Date: Nov. 30, 2012

(87) PCT Pub. No.: WO2011/152788
PCT Pub. Date: Dec. 8, 2011

(65) Prior Publication Data
US 2013/0068671 A1    Mar. 21, 2013

(30) Foreign Application Priority Data
Jun. 3, 2010    (SE) ...................................... 1050565

(51) Int. Cl.
*B01D 15/22*    (2006.01)
*B01D 15/18*    (2006.01)
(Continued)

(52) U.S. Cl.
CPC ......... *B01D 15/22* (2013.01); *B01D 15/1864* (2013.01); *F16L 55/00* (2013.01);
(Continued)

(58) Field of Classification Search
CPC .............. B01D 15/1871; B01D 24/005; B01D 24/002; G01N 30/6039; G01N 30/6043
(Continued)

(56) References Cited

U.S. PATENT DOCUMENTS

| | | | |
|---|---|---|---|
| 3,254,479 | A | 6/1966 | Goeschl |
| 3,322,337 | A | 5/1967 | Rudolf |

(Continued)

FOREIGN PATENT DOCUMENTS

| | | |
|---|---|---|
| CN | 1511256 | 7/2004 |
| CN | 200951333 | 9/2007 |

(Continued)

OTHER PUBLICATIONS

Gray, M. J., et al., Journal of Chromatography A, 1096 (2005) 92-100.

(Continued)

*Primary Examiner* — Krishnan S Menon
*Assistant Examiner* — Waqaas A Ali
(74) *Attorney, Agent, or Firm* — Wood IP LLC

(57) ABSTRACT

A parallel assembly (2; 11; 51) of chromatography column modules (3a,b,c; 13a,b,c; 53a,b,c, 90a, b) connected in a rigid housing (21; 61), the assembly having one common assembly inlet (15; 55) and one common assembly outlet (17; 57), each column module comprising a bed space (29) filled with chromatography medium and each column module comprises integrated fluid conduits which when the column module is connected with other column modules in the rigid housing are adapted to connect the bed space (29) of the column module with the assembly inlet (15; 55) and the assembly outlet (17; 57), wherein the total length and/or volume of the fluid conduit from the assembly inlet to one bed space together with the length and/or volume of the fluid conduit from the same bed space to the assembly outlet is substantially the same for all bed spaces and modules installed in the parallel assembly.

12 Claims, 13 Drawing Sheets

(51) Int. Cl.
*G01N 30/46* (2006.01)
*F16L 55/00* (2006.01)
*G01N 30/60* (2006.01)

(52) U.S. Cl.
CPC ......... *G01N 30/461* (2013.01); *G01N 30/466* (2013.01); *G01N 30/6004* (2013.01); *B01D 15/1885* (2013.01); *Y10T 29/49826* (2015.01)

(58) Field of Classification Search
USPC .................. 210/635, 656–659, 198.2–198.3
See application file for complete search history.

(56) References Cited

U.S. PATENT DOCUMENTS

| | | | |
|---|---|---|---|
| 3,763,879 A * | 10/1973 | Jaworek | B01L 3/5021 137/268 |
| 4,155,846 A * | 5/1979 | Novak | G01N 30/6069 210/198.2 |
| 5,817,528 A * | 10/1998 | Bohm et al. | 436/529 |
| 6,306,200 B1 | 10/2001 | Yu | |
| 6,911,151 B1 | 6/2005 | Muller-Kuhrt et al. | |
| 7,261,812 B1 | 8/2007 | Karp et al. | |
| 8,506,802 B1 | 8/2013 | De Los | |
| 9,120,037 B2 | 9/2015 | De Los | |
| 2002/0187557 A1 | 12/2002 | Hobbs et al. | |
| 2003/0094415 A1* | 5/2003 | Tanimura | 210/656 |
| 2006/0118471 A1* | 6/2006 | Vidalinc | B01D 15/22 210/198.2 |
| 2007/0193595 A1* | 8/2007 | Haruki | A24B 15/24 131/297 |
| 2007/0204749 A1 | 9/2007 | Adkins | |
| 2008/0237132 A1 | 10/2008 | Hotier et al. | |
| 2009/0145851 A1* | 6/2009 | Witt | 210/741 |
| 2009/0321338 A1* | 12/2009 | Natarajan | 210/198.3 |
| 2012/0118807 A1 | 5/2012 | Natarajan | |
| 2013/0228501 A1 | 9/2013 | Lefebvre et al. | |
| 2014/0263012 A1 | 9/2014 | Gebauer | |
| 2014/0339170 A1 | 11/2014 | De Los | |

FOREIGN PATENT DOCUMENTS

| | | |
|---|---|---|
| DE | 203 14 328 | 12/2003 |
| EP | 2577289 A1 | 4/2013 |
| FR | 2645965 A1 * | 10/1990 |
| FR | 2681138 A1 * | 9/1991 |
| FR | 2 681 138 | 3/1993 |
| JP | 05-339297 | 12/1993 |
| WO | WO 2003/044526 | 5/2003 |
| WO | WO 2004/101151 | 11/2004 |
| WO | 2009157852 | 12/2009 |
| WO | 2011/152788 A1 | 8/2011 |

OTHER PUBLICATIONS

EP Search Report dated Nov. 7, 2013 issued on corresponding EP application No. 11790092.8.
Search Report dated Mar. 4, 2014 Issued on Corresponding CN Application No. 201180026967.1.
Gray, M., et al., Journal of Chromatography A, vol. 1096 (2005) pp. 92-100.
International Search Report and Written Opinion Received for PCT Patent Application No. PCT/SE2011/050681, dated Sep. 22, 2011, 11 Pages.
International Preliminary Report on Patentability Received for PCT Patent Application No. PCT/SE2011/050681, dated Dec. 13, 2012, 8 Pages.
Restriction Requirement Received for U.S. Appl. No. 14/290,357, dated May 1, 2015, 7 Pages.
Non Final office Action Received for U.S. Appl. No. 14/290,357, dated May 21, 2015, 20 Pages.
Final Office Action Received U.S. Appl. No. 14/290,357, dated Sep. 17, 2015, 20 Pages.
Non Final office Action Received for U.S. Appl. No. 14/290,357, dated Mar. 24, 2016, 21 Pages.
Final office Action Received for U.S. Appl. No. 14/290,357, dated Jul. 21, 2016, 21 Pages.
Non Final office Action Received for U.S. Appl. No. 14/290,357, dated Nov. 15, 2016, 22 Pages.
Final office Action Received for U.S. Appl. No. 14/290,357, dated Mar. 21, 2017, 23 Pages.
Notice of Allowance Received U.S. Appl. No. 14/290,357, dated Jul. 21, 2017, 7 Pages.

* cited by examiner

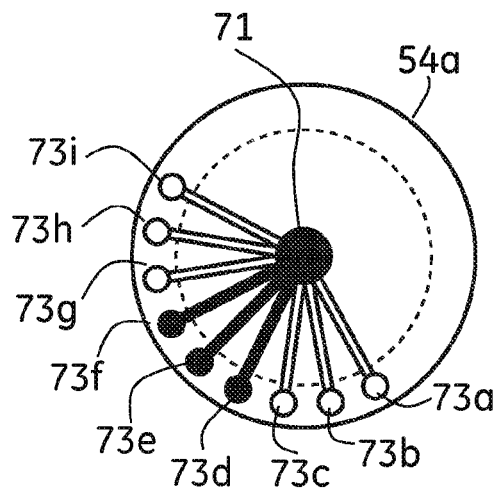
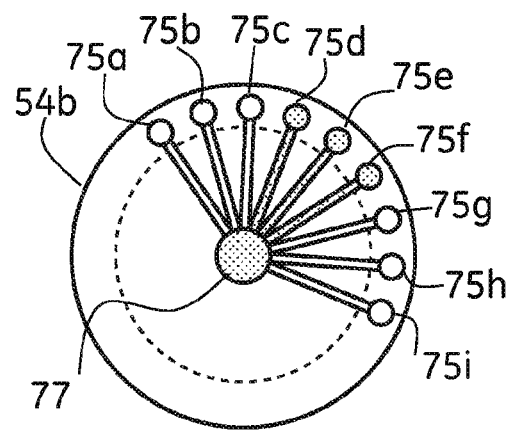
FIG. 6a            FIG. 6b
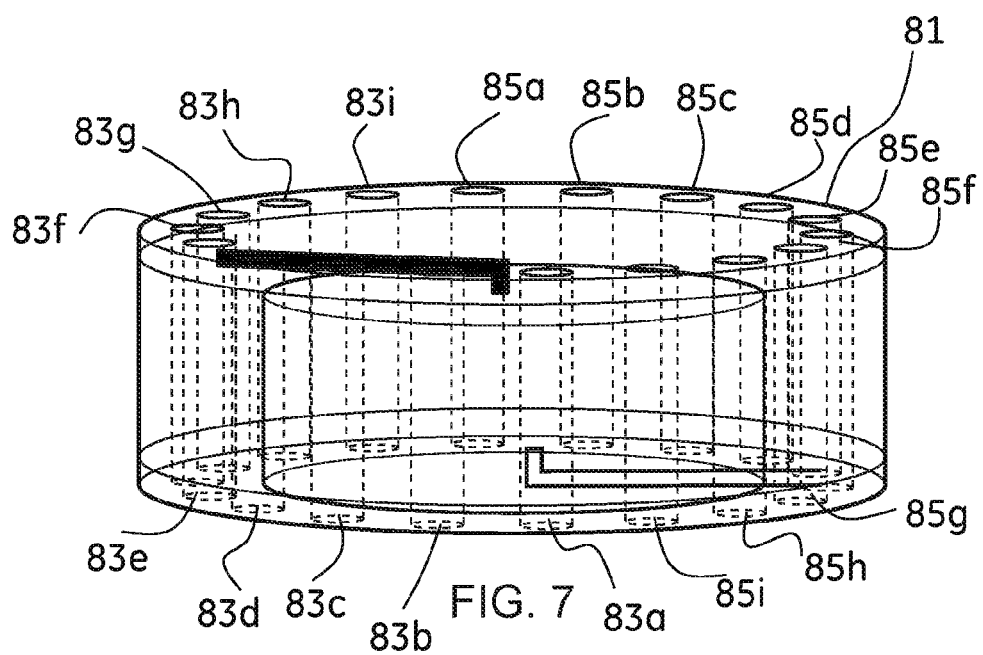
FIG. 7

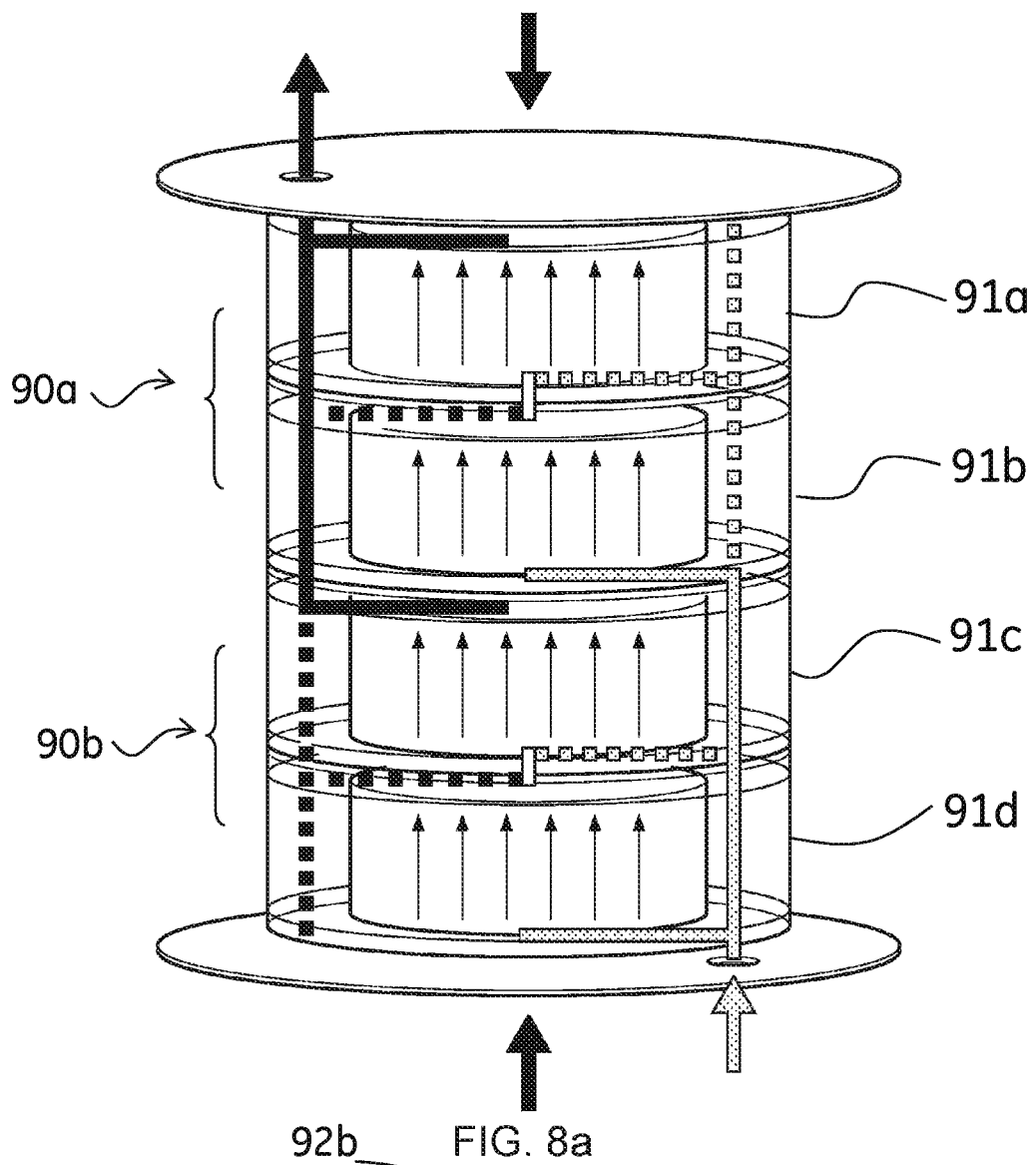
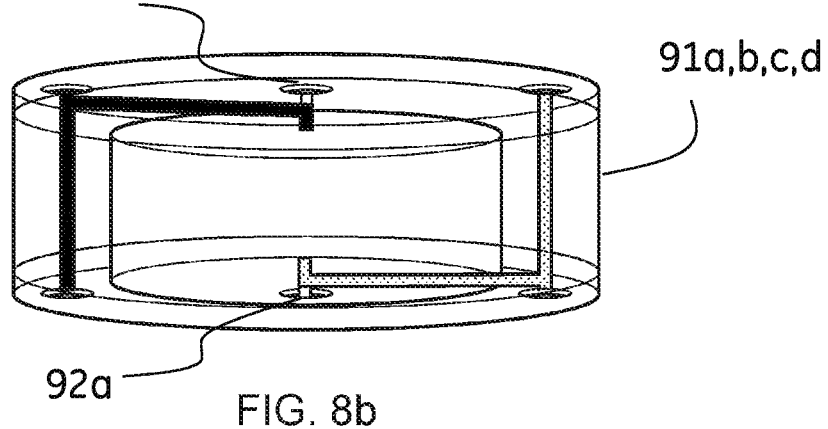
FIG. 8a
FIG. 8b

PARALLEL ASSEMBLY OF CHROMATOGRAPHY COLUMN MODULES

CROSS-REFERENCE TO RELATED APPLICATIONS

This application is a filing under 35 U.S.C. 371 of international application number PCT/SE2011/050681, filed Jun. 1, 2011, published on Dec. 8, 2011 as WO 2011/152788, which claims priority to application number 1050565-9 filed in Sweden on Jun. 3, 2010.

TECHNICAL FIELD OF THE INVENTION

The present invention relates to a parallel assembly of chromatography column modules, a chromatography column module adapted to be used in a parallel assembly, a rigid housing adapted to hold any number of chromatography column modules and to a method for connecting chromatography column modules in a rigid housing.

BACKGROUND OF THE INVENTION

The use of separation modules, such as chromatography columns or cartridges, in a parallel configuration has a potential to increase flexibility in pilot and process scale bio-manufacturing. Flexibility is increased by the ability to build a larger system of required capacity from a number of standardized modules. However, there are a number of problems associated with this concept when using chromatography columns of prior art.

One of the problems is that space requirements increase when using an arrangement of multiple columns configured in parallel, hereby increasing the overall footprint of the equipment when compared to the use of a single larger standard column. Another problem is that overall cost increases significantly when using a number of smaller prior art columns in parallel configuration compared to using a single large column. This problem is related to the fact that all individual columns of prior art that would be used in a parallel configuration need to provide mechanical rigidity in order to comply with design standards and pressure equipment directives. Yet another problem is that fluid manifolds are required to connect the multiple columns in parallel, hereby increasing the overall complexity and cost of the installation. Complexity in fluid manifolds connecting prior art columns in parallel is also increased by the fact that essentially the same hold-up volume and pressure loss is required over all parallel fluid lines in the parallel configuration to enable the same residence time distribution over all columns in the parallel configuration required to achieve good overall chromatographic efficiency that is as good as when using a single column.

SUMMARY

One object of the invention is to provide a flexible and scalable chromatography system.

This is achieved by a parallel assembly according to claim 1, by a chromatography column module according to claim 6 and by a rigid housing according to claim 17 and by a method according to claim 18. Hereby a suitable number of column modules can be connected inside the rigid housing forming a chromatography system and fluid connections provided in the column modules will be connected so no extra fluid manifolds are needed. Furthermore, in parallel connection mode, the total length of the inlet manifold and the outlet manifold to each module of the parallel assembly is the same which will assure a good performance. This parallel assembly will also provide a compact design which will give a low footprint.

Furthermore, this parallel assembly will provide a flexible system where smaller units that can be handled manually are connected in parallel to provide "one" larger column. Still further the rigid housing of the parallel assembly provides a system where the separate column modules do not need stiff end plates resisting high fluid pressures themselves. Hereby a reduction in cost and weight is achieved.

In one embodiment of the invention an adjustable flow restrictor is provided in each chromatography column module. Hereby a good performance is achieved by synchronised hydraulic resistance (i.e. same residence time over all modules).

In one embodiment a sensor of the same type is provided to each column module. Hereby a parallel system is achieved that enables verification and qualification.

Suitably the column modules are disposable.

In one embodiment of the invention aseptic films are provided to the fluid connections between the chromatography column modules and between the chromatography column modules and the rigid housing. The films are adapted to be removed two and two together after assembly of the system. Hereby the separate modules can be treated in a non sterile environment while the contents of the modules and the fluid connections still are kept aseptic.

In one embodiment of the invention the chromatography column modules are filled with dry chromatography medium.

Further suitable embodiments are described in the dependent claims.

BRIEF DESCRIPTION OF THE DRAWINGS

FIG. 4a shows schematically one end piece of a column module that has been provided by moulding methods according to one embodiment of the invention.

FIG. 4b shows schematically one example of configurability in the form of a puncture web at the end piece of a column module.

FIGS. 6a and b show schematically a pair of fluid distribution modules to be used in the embodiment of the invention shown in FIG. 5.

FIG. 7 shows schematically integrated tube fluid conduits in one chromatography column module to be used in the embodiment of the invention shown in FIG. 5.

FIG. 8a shows schematically another embodiment of the invention where two chromatography column modules are connected in parallel where the chromatography column modules in this embodiment each comprise two serially connected chromatography column submodules.

FIG. 8b shows schematically a chromatography column submodule to be used in the embodiment shown in FIG. 8a.

FIG. 9b is a flow chart of the method for adjusting hydraulic resistance in the flow paths according to the embodiment of the invention shown in FIG. 9a.

FIG. 13b shows schematically a chromatography column module to be used in the system shown in FIG. 13a.

DETAILED DESCRIPTION OF THE EMBODIMENTS

Figure 1:
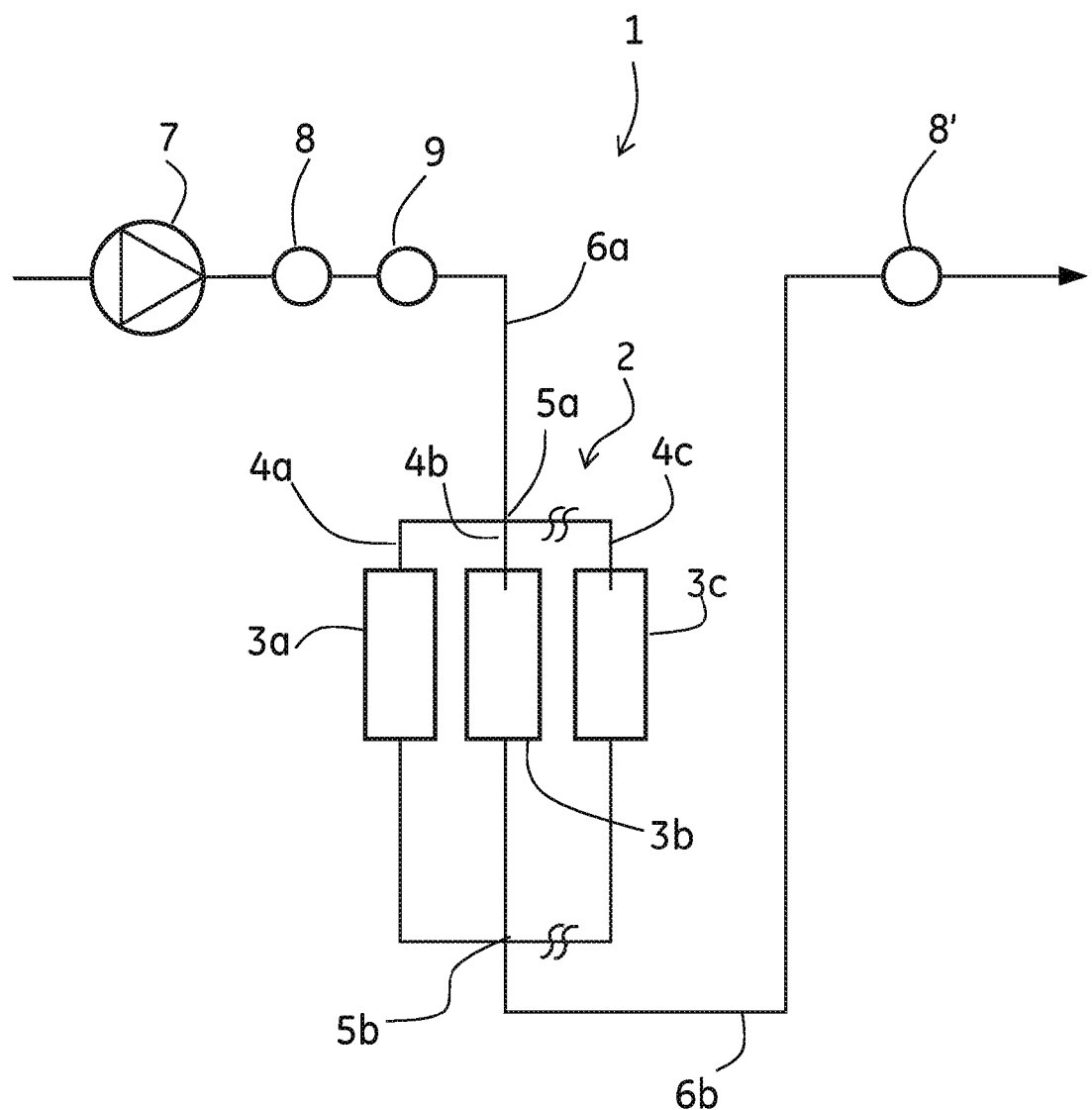
FIG. 1 shows schematically a parallel arrangement of three chromatography column modules according to one embodiment of the invention.

FIG. 1 shows schematically a flow scheme for a separation system 1 comprising a parallel assembly 2 of three chromatography column modules 3a, 3b, 3c according to one embodiment of the invention. The number of parallel connected column modules can also be two or more than three. The parallel assembly 2 comprises in this example three parallel fluid paths 4a, 4b, 4c. Each fluid path 4a, 4b, 4c comprises one column module 3a, 3b, 3c. One assembly inlet 5a defines a common fluid inlet to the parallel assembly 1 and one assembly outlet 5b defines a common fluid outlet from the parallel assembly 2. The separation system 1 comprises further an inlet fluid path 6a connecting to the assembly inlet 5a and an outlet fluid path 6b connecting to the assembly outlet 5b. The inlet fluid path 6a comprises in this embodiment a pump 7, a flow meter 8 and a pressure sensor 9. Alternatively the flow meter could be positioned downstream the parallel assembly 3, which is shown as flow meter 8'. In another alternative embodiment, the pump 7 in the separation system is a pump of metering type, hereby allowing for an a priori determination of delivered flow rate by calculation from a number of pump revolutions, a displaced volume or similar. In this alternative, flow meters 8 and 8' described above may be omitted as the flow rate is pre-determined. Yet another alternative embodiment of the system may employ a calibration curve for the system pump to avoid the need for a flow meter in the system.

Figure 2:
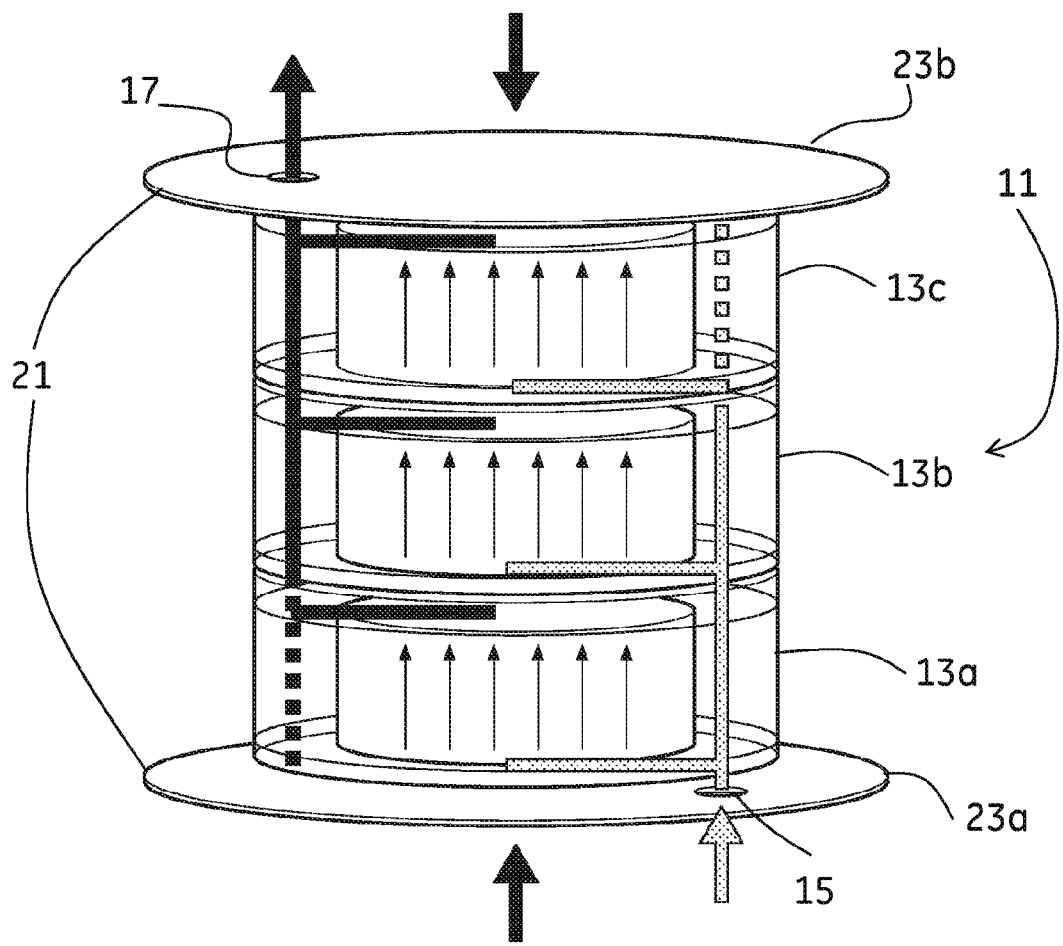
FIG. 2 shows schematically a parallel arrangement of three chromatography column modules in a rigid housing according one embodiment of the invention.

The parallel assembly 2 of FIG. 1 can be configured in an embodiment of the invention as shown in FIG. 2. In FIG. 2 three chromatography column modules 13a, 13b, 13c are arranged in a parallel assembly 11 in a rigid housing 21 according to one embodiment of the invention. The number of column modules can of course vary. The rigid housing 21 is represented as a compression frame 21 where the column modules 13a, 13b, 13c are positioned in between two rigid end plates 23a, 23b of the compression frame 21. An assembly inlet 15 is provided in one of the end plates 23a and an assembly outlet 17 is provided in the other end plate 23b. Assembly inlet 15 and assembly outlet 17 are suitably arranged through an opening in the rigid end plates 23a and 23b respectively such that the rigid end plates have no direct fluid contact. When the chromatography column modules 13a, 13b, 13c are assembled in the compression frame 21 and a compression force has been applied the assembly inlet 15 and the assembly outlet 17 has direct fluid communication with fluid conduits provided in the column modules 13a, 13b, 13c.

Figure 3A:
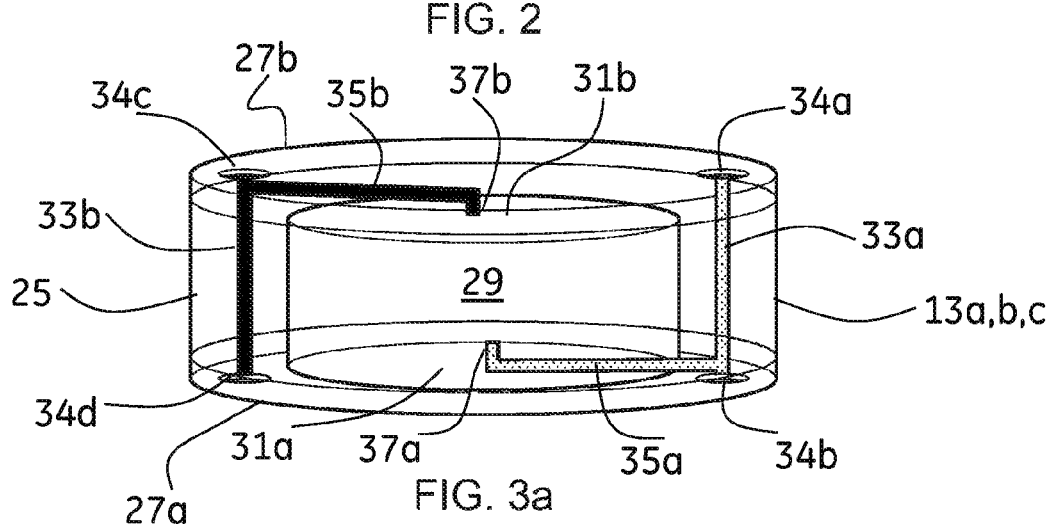
FIG. 3a shows schematically a chromatography column module for installation in the parallel assembly according to the embodiment shown in FIG. 2.

One chromatography column module 13a, 13b, 13c adapted to be used in a parallel assembly 11 according to the embodiment shown in FIG. 2 is schematically shown in FIG. 3a. The column module 13a, 13b, 13c comprises a tube 25 and one lower and one upper end piece 27a, 27b. The tube 25 and the end pieces 27a, 27b together define a bed space 29 filled with chromatography medium. A bottom distribution system 31a is provided in the bottom of the bed space 29 and a top distribution system 31b is provided at the top of the bed space 29. The tube 25 comprises in this embodiment one or two integrated fluid conduits 33a, 33b. The fluid conduits 33a and 33b ends in fluid connections 34a, b, c, d at the positions aimed for connection to a second and third column module above or below the module. The fluid connections 34a, b, c, d, are suitably configured with sealing means. The sealing means are suitably made from gaskets that engage in a fluid tight sealing arrangement as soon as the modules are stacked on top of each other and/or compressed against each other by help of the compression frame.

From FIG. 2 it is clear that only the column module 13b that is positioned in the middle of the parallel assembly 11 need two fluid conduits 33a, 33b in the tube 25 that connect at both inlet and outlet side to the two other column modules 13a and 13c positioned above and below the middle column module 13b.

To avoid dead legs in the fluid conduit in each of the column modules that are to be positioned uppermost and lowermost in the parallel assembly of FIG. 2, the outlet fluid conduit 33b in the column tube 25 of the lower module 13a is suitably shut off. Further, the inlet conduit 33a in the column tube 25 of the uppermost module 13c is suitably shut off. This can be achieved by adapting the respective fluid conduits 33a, 33b with plugs that seal off the respective fluid conduit. Alternatively, these fluid conduits can be configured by providing puncture webs or plugs in the end pieces of the column modules, which is further described in relation to FIGS. 4a and 4b.

The lower end piece 27a further comprises a fluid conduit 35a connecting a bed space inlet 37a with the tube fluid conduit 33a. The upper end piece 27b correspondingly comprises a fluid conduit 35b connecting a bed space outlet 37b with the tube fluid conduit 33b. Hereby, now referring to FIG. 2, each column module 13a, 13b, 13c comprises integrated fluid conduits 33a, 33b, 35a, 35b which when the column module 13a, 13b, 13c is connected with other column modules 13a, 13b, 13c in the rigid housing 21 are adapted to connect the bed space 29 of the column module 13a, 13b, 13c with the assembly inlet 15 and the assembly outlet 17, wherein the total length and/or volume of the fluid conduit from the assembly inlet 15 to one bed space 29 together with the length and/or volume of the fluid conduit from the same bed space 29 to the assembly outlet 17 is substantially the same for all bed spaces and modules 13a, 13b, 13c installed in the parallel assembly. Substantially is used here to make it clear that also small differences in length/volume should fall under this patent. In one embodiment of the invention a difference of less than 20% is acceptable. The overall goal of having the same length and or volume of the fluid conduits is to achieve substantially the same residence over all parallel fluid paths in the assembly.

Substantially the same is used here just to make it clear that it is hard to achieve exactly the same residence time distribution and also small differences should be covered by this invention.

In FIG. 2 it can be seen that the assembly inlet 15 and the assembly outlet 17 are connected to the end plates in a substantially axial way. However, the inlet and the outlet may be connected to the end plates also in a substantially radial way. Also, a separate fluid distribution module may be provided to connect one or more inlets, outlets and fluid conduits. One example of such embodiment is described later in connection with FIG. 5.

Figure 3B:
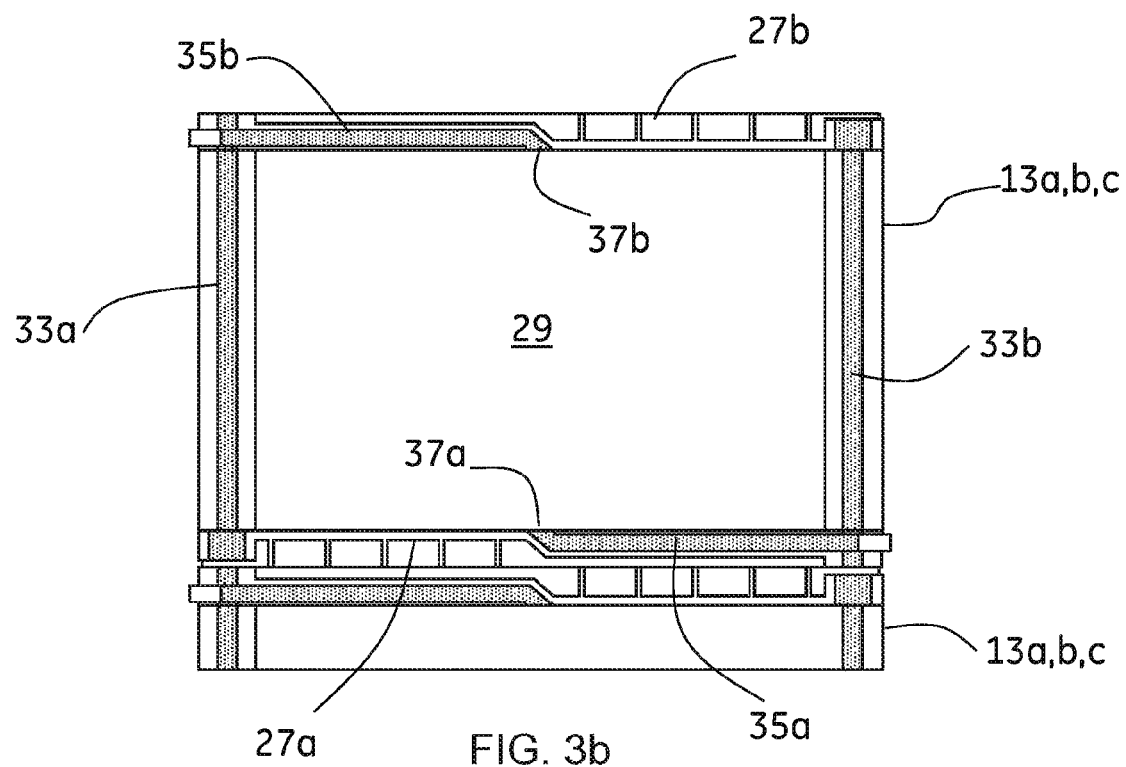
FIG. 3b shows the column module of FIG. 3a in a cross sectional side view.

In FIG. 3b the chromatography column module of FIG. 3a is shown in a cross sectional side view. The parts are numbered correspondingly with FIG. 3a. In this Figure it is also shown how the column module is connected to another column module at its lower end (referring to the direction of the drawing). The lower and upper end pieces 27a, 27b are shown with structures (similar structures are also shown more clearly in FIG. 3c) for increase of stiffness and mechanical stability that result from a molding manufacturing process which is a suitable manufacturing method. Examples of suitable molding processes are injection molding and extrusion molding, but the processes are not limited to these and any other molding process may be used. As molding techniques generally are restricted to structures of limited wall thickness (<10 mm), the application of structural elements is suitable for improving the mechanical rigidity to a minimum level. The top and bottom surface of the reinforcement structures are suitably covered by a flat end plate or film to provide a clean and flush surface, which is not shown. According to one objective of the invention, the end pieces have mechanical rigidity that is sufficient for transport and installation of the modules in the rigid frame. The end pieces do not have sufficient rigidity for supporting an operation of the column modules at typical operational fluid pressures, which is why the assembling of the modules in the rigid frame is required. In one embodiment, the end pieces 27a, 27b have not sufficient rigidity to support a mechanical pre-compression of the chromatography medium as a result of a column packing process. The column packing process may be the result of a swelling of chromatography medium within the column space or it may be the result of mechanical stress or fluid flow stress and fluid pressure applied when consolidating the chromatography medium in the bed space.

The limited mechanical rigidity of the end pieces 27a, 27b of the chromatography modules serves another objective of the invention, which is to reduce cost.

Figure 3C:
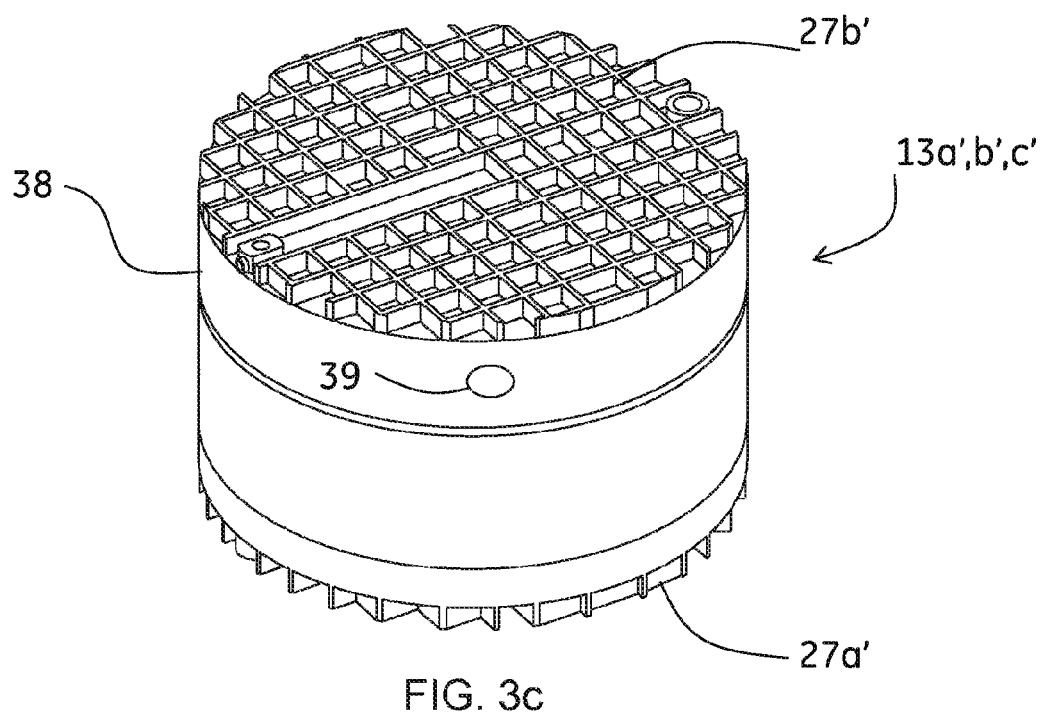
FIG. 3c shows the column module of FIG. 3a in a perspective view.

The chromatography module 13a, 13b, 13c is suitably fitted with an opening to fill the bed space 29 with chromatography medium. This opening may extend through one of the end pieces 27a, 27b or through the column tube 25. The opening is plugged and sealed after filling of the bed space 29. An alternative embodiment of a column module is shown in FIG. 3c. Here, an upper end piece 27b' has been extended with a column tube section 38. The column tube section 38 has been adapted with an opening 39 that is aimed for filling of chromatography medium into the bed space.

In one embodiment the chromatography medium is dry chromatography media. In that case the dry chromatography medium is introduced through the port in each column module. Suitably the amount of dry chromatography medium filled to the column is such that the volume of the swollen medium after liquid has been added would occupy a larger volume than the volume of the bed space when being not confined by the bed space in the column modules. In a typical embodiment, the volume of swollen medium when not confined by the walls and volume of the bed space would be 2-30% larger than the volume of the bed space and be compressed accordingly in the column module. Preferably, the volume of swollen medium when not confined by a bed space of the module would be 5-20% larger than the volume of the bed space in the module. Hereby, the porous chromatographic bed formed by the swollen chromatography medium becomes pre-compressed which is typically a pre-requisite for achieving a packed bed with a good chromatographic efficiency and that is stable over time and a larger number of process cycles, respectively. Suitably the amount of dry chromatography medium filled into the chromatography module corresponds to a dry medium volume somewhat lower than the volume of the bed space in the column module. Hereby, no mechanical force or stress is applied upon the chromatography module other than the weight of the dry chromatography medium which has to be supported by the chromatography module. This embodiment allows for a transport and installation of the dry filled chromatography modules without the risk of deformation when using not fully rigid end pieces during these steps. After installation of the dry filled modules in the rigid frame, liquid can be applied and the dry gel can be swollen to a larger volume. The rigid frame will counteract the load and internal pressure from the re-swollen medium and prevent the end pieces of the chromatographic modules to deform.

In another embodiment, the chromatography modules are installed in the frame without being filled with chromatography medium. After providing mechanical rigidity to the modules by installation in the rigid frame, the modules can be filled through an opening in the module as for example port 39. As mechanical rigidity is given, the column may be filled with a suspension of chromatography medium that is preferably compressed by introducing the suspension at high flow rate and high pressure, hereby causing a pre-compression of the packed bed. Alternatively, the chromatographic medium may be introduced dry in a first step and re-swollen in a second step.

In another embodiment, the chromatography module is not provided with an opening for filling of chromatography medium. Instead, the medium is filled into the module before adapting an end piece to the module. The end piece may suitably be secured and sealed by clamping means, a threaded, welding techniques or similar.

Figure 4A:
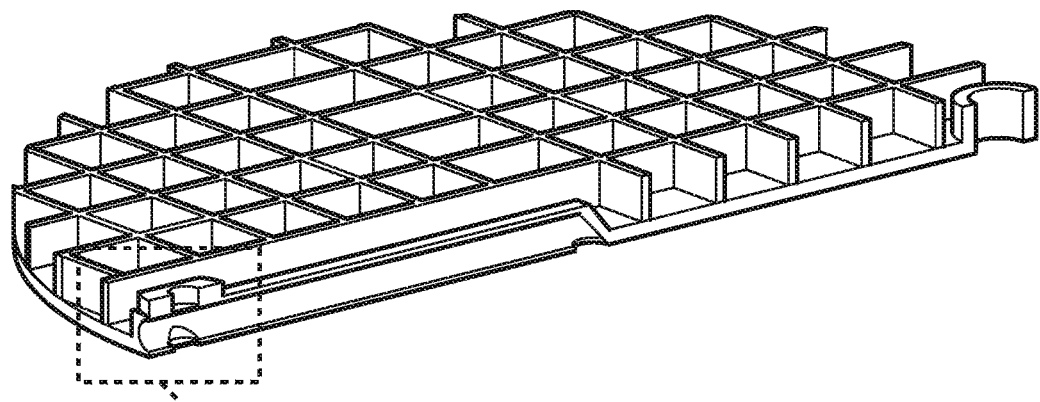
FIGS. 4a-4b show detailed views on the chromatography column module shown in FIG. 3.
Figure 4B:
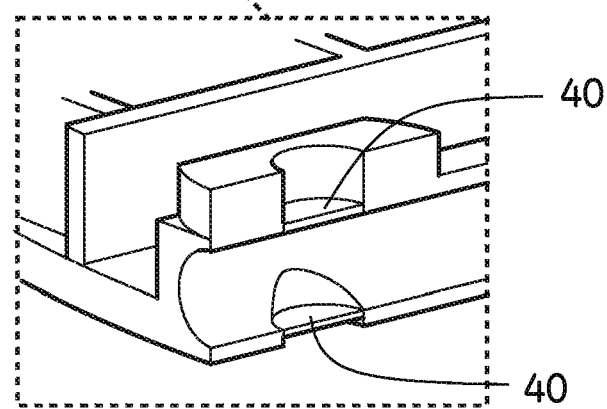

FIGS. 4a-4b show detailed views on the chromatography column module shown in FIG. 3. FIG. 4a shows schematically one half of an end piece of a column module that has been provided by moulding methods according to one embodiment of the invention. FIG. 4b shows schematically one example of configurability in the form of a puncture web 40.

The configurability of the end pieces can be provided in different ways. Suitably one single type of end piece (or at least a single molding tool) which can be easily configured for molding or during post manufacturing, during final assembly or even at the point of use is provided. The following routes can be selected:
 a) Inserts during molding are placed in the tool to achieve the desired design, resulting in different molded parts
 b) One single molded part is designed with open flow junctions and multiple inserts (probably with O-ring seals) are then fitted into these open junctions to configure the part as needed
 c) One single molded part is designed such that puncture webs are removed depending on multiple configurations needed.

The routes for achieving configurability during post-manufacture of the end pieces discussed above are preferable for overall cost-efficiency. A further route for configurability is the inclusion of valves in the fluid conduits of the chromatography module that could be configured at the point of use. Hereby, a single standard configuration of the module and its fluid conduits can be provided and the actual configuration required for the final assembly and be determined and achieved at the point of use and during assembly and installation of the parallel assembly, respectively. Suitable valves are especially rotary valves as they are inexpensive and can be configured such that for multiple functions are comprised in a single valve, like for example blocking of a fluid conduit, opening of a fluid conduit and also connecting two or more fluid conduits.

The tube 25 of the chromatography column modules is suitably extruded. Advantages with extruding the tubes are for example cost reduction, no machining of built-in fluid conduits required (cost reduction) and good surface finish. By nature of the extrusion process, long tube elements are produced in the extrusion process that are cut to provide the column tube elements required for the specific chromatography modules. By cutting the tube elements to appropriate length, column modules with different heights of the bed space and chromatographic packing can easily be accommodated.

The tube 25 of the chromatography column modules may also be manufactured such that the tube 25 comprises or is provided from multiple pieces or segments, such as two pieces or segments, which may be equal in size or have different sizes. The pieces may be for example injection molded or extruded and different manufacturing methods may be selected for the individual tube segments depending on required functionality. As shown in FIG. 3a, one piece or segment of the tube may for example be part of an end piece and provided by injection molding methods, for example. It could be combined with another tube segment provided by extrusion methods to form the column tube and joined with an opposite end piece provided by injection molding, for example. Separation modules of different bed height may be provided by combining a number of tube segments as mentioned above to achieve a desired total bed height and tube length, respectively, in a modular fashion. The two pieces may be then coupled together to form the tube 24 by using suitable means, such as for example welding or screws or adhesive. Welding methods such as mirror welding, laser welding or ultrasonic welding are preferable techniques for joining mentioned segments with each other and with other column parts such as end plates.

Suitably the method of assembly for the end pieces and column tube to build a chromatography module comprises welding. Other alternatives are mechanical methods like clamping, threads, etc. that require sealing elements (O-rings). Welding is preferred from a cost perspective especially for a disposable product. Welding is probably also preferred with regard to the robustness achieved.

Figure 5:
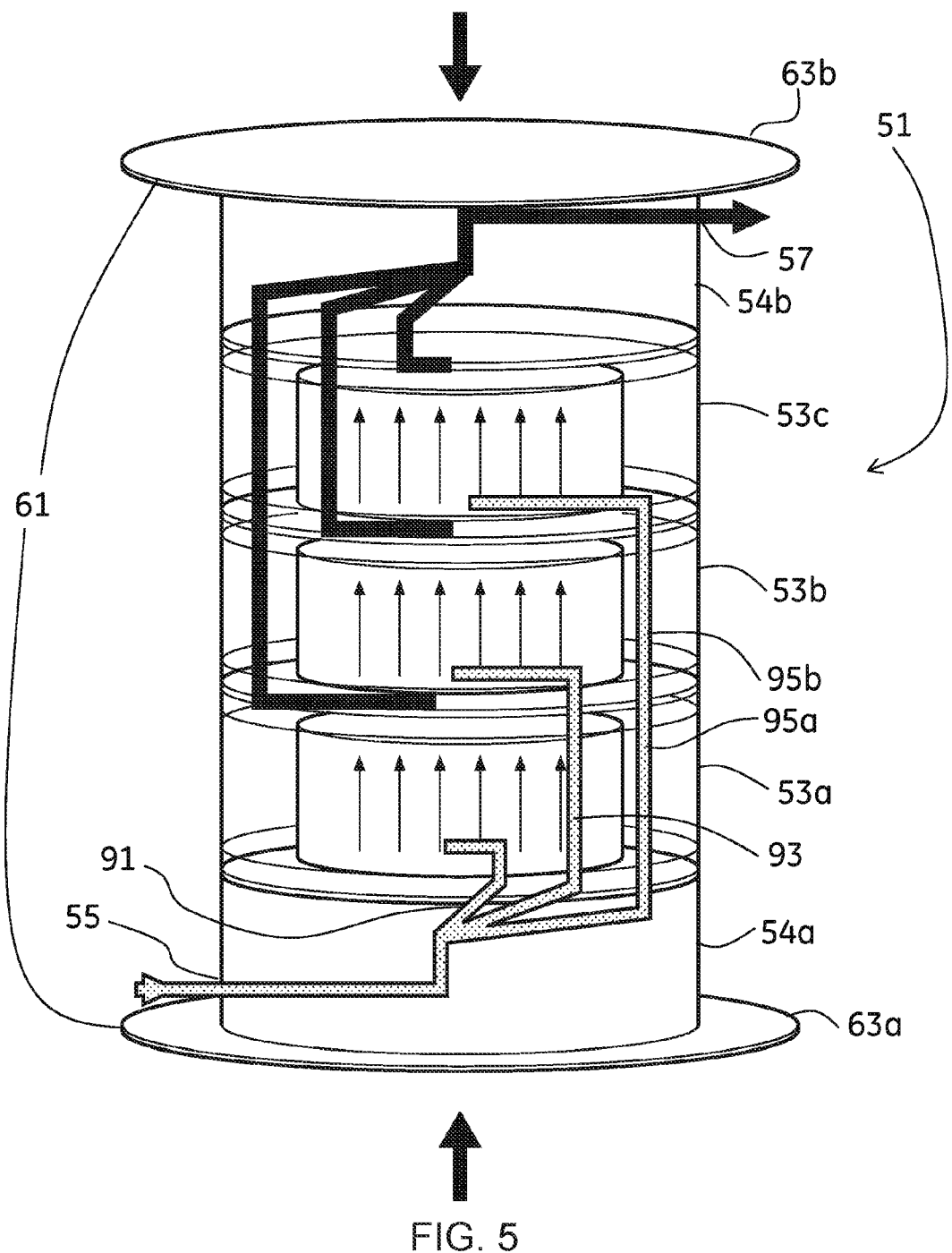
FIG. 5 shows schematically a parallel arrangement of three chromatography column modules according to another embodiment of the invention.

FIG. 5 shows schematically a parallel arrangement 51 of three chromatography column modules 53a, 53b, 53c according to another embodiment of the invention. According to this embodiment there is also provided one fluid distribution module 54a, 54b on each side of the stack of connected column modules 53a, 53b, 53c but still in between two rigid end plates 63a, 63b defining a rigid housing 61. An assembly inlet 55 is provided in one of the distribution modules 54a and an assembly outlet 57 is provided in the other of the two distribution modules 54b.

FIGS. 6a and b show schematically a connection face of a pair of fluid distribution modules 54a, 54b to be used in the embodiment of the invention shown in FIG. 5. The connection faces should be connected to the stack of chromatography column modules. The assembly inlet 55 is connected to a central fluid connection 71 of one of the distribution modules 54a. The central fluid connection 71 can be connected to an optional number of peripheral fluid connections 73a, b, c, d, e, f, g, h, i. Here, the maximum number of peripheral fluid connections is shown to be 9. Suitably these should be provided over at the most 180 degrees of the periphery. Hereby, with this embodiment of the invention a maximum number of 9 column modules can be connected in parallel. However, by the use of for example puncture webs as described above, suitably only the number of used fluid connections are connected to the central fluid connection 71 and thereby in use. In this shown embodiment three column modules 53a, 53b, 53c are connected in the rigid housing and hereby only three of the peripheral fluid connections 73d, e, f are connected to the central fluid connection 71. The other fluid distribution module 54b, i.e. the one positioned in the other end of the stack of column modules, suitably has a corresponding number of peripheral fluid connections 75a, b, c, d, e, f, g, h, i, distributed on the opposite side of the circle over 180 degrees. Suitably only a number corresponding to the actual number of connected column modules of the peripheral fluid connections 75d, e, f, are connected to a central fluid connection 77.

In one embodiment of the invention, the tube may comprise built-in prepared fluid connections having different diameters. Depending on the fluid volumes and the size of the liquid conduits needed in a process, a fluid connection with suitable diameter is used. For example, in case there are more than 3 modules in the column, larger fluid connections for larger fluid conduits may be used and in case there are 1-3 modules in the column, smaller fluid connections for smaller fluid conduits may be used by rotating the end pieces of the module to a desirable fluid connection position.

FIG. 7 shows a cross section of a column module tube 81 of a column module 53a, 53b, 53c to be used in the embodiment shown in FIGS. 5 and 6. The column module tube 81 comprises a number of integrated fluid conduits 83a, b, c, d, e, f, g, h, i, 85a, b, c, d, e, f, g, h, i corresponding to the number of peripheral fluid connections of the distribution modules 54a, 54b used in this embodiment. Each fluid conduit ends up in one fluid connection on each side of the column module. The end pieces of the column modules 53a, 53b, 53c will be configured to open up to suitable fluid conduits in the tube. Furthermore, fluid conduits are provided from one of fluid conduit 83a-i and one of fluid conduits 85a-i to the inlet and the outlet of the bed space respectively In FIG. 5 it is shown that for example the first column module 53a has one direct fluid path 91 to the bed space inlet and one fluid path 93 leading to the inlet of the second module 53b and one fluid path 95a connecting with a fluid path 95b of the second module 53b. Corresponding design is provided on the outlet side but preferably using fluid conduits on the other side of the periphery in the module tubes. If more than three column modules are to be connected in parallel according to the invention more of the column tube fluid conduits will also need to be used.

FIG. 8a shows schematically another embodiment of the invention where two chromatography column modules 90a, 90b are connected in parallel. In this embodiment of the invention the chromatography column modules 90a, b each comprises two serially connected chromatography column submodules 91a, b, c, d. The number of serially connected submodules in each chromatography column module 90a, b could of course be any number, for example two, three or four. FIG. 8b shows schematically a chromatography column submodule 91a, b, c, d to be used in the embodiment shown in FIG. 8a. The chromatography column submodule 91a, b, c, d used in this embodiment of the invention needs to have possibilities for fluid connection also directly in to the inlet and outlet to enable serial connection with a neighbouring submodule. In this embodiment it is shown to be a fluid connection 92a, b in the middle of the chromatography column module, however the connection could be placed somewhere else than in the middle if a fluid conduit is provided to the inlet and outlet respectively.

In order to define the overall configuration of the assembly as to achieve a desired parallel and/or serial configuration of chromatography modules and/or chromatography submodules, configurability for opening or closing at least one fluid conduit in at least one chromatography module or chromatography submodule is required. The configuration of the fluid conduit(s) in a chromatography module or submodule is preferably provided by configurable end pieces as shown in FIG. 4a and as discussed in the text above related to configurability and FIGS. 4a and 4b.

Other alternatives for adapting a chromatography submodule for a serial configuration are changes in orientation, for example by turning a module up-side down, hereby mating outlet connection of a first module with the inlet connection of a second module or by rotating a module in regard to a second module.

In one embodiment of the invention adjustable flow restrictors are further provided to each one of the column modules. These adjustable flow restrictors can be used to calibrate the flow resistance in the different fluid paths each comprising one column module and one adjustable flow restrictor. The purpose is to provide a system where each fluid path has the same hydraulic resistance. This will give a uniform flow over the different column modules in the assembly which will improve the separation efficiency.

Figure 9A:
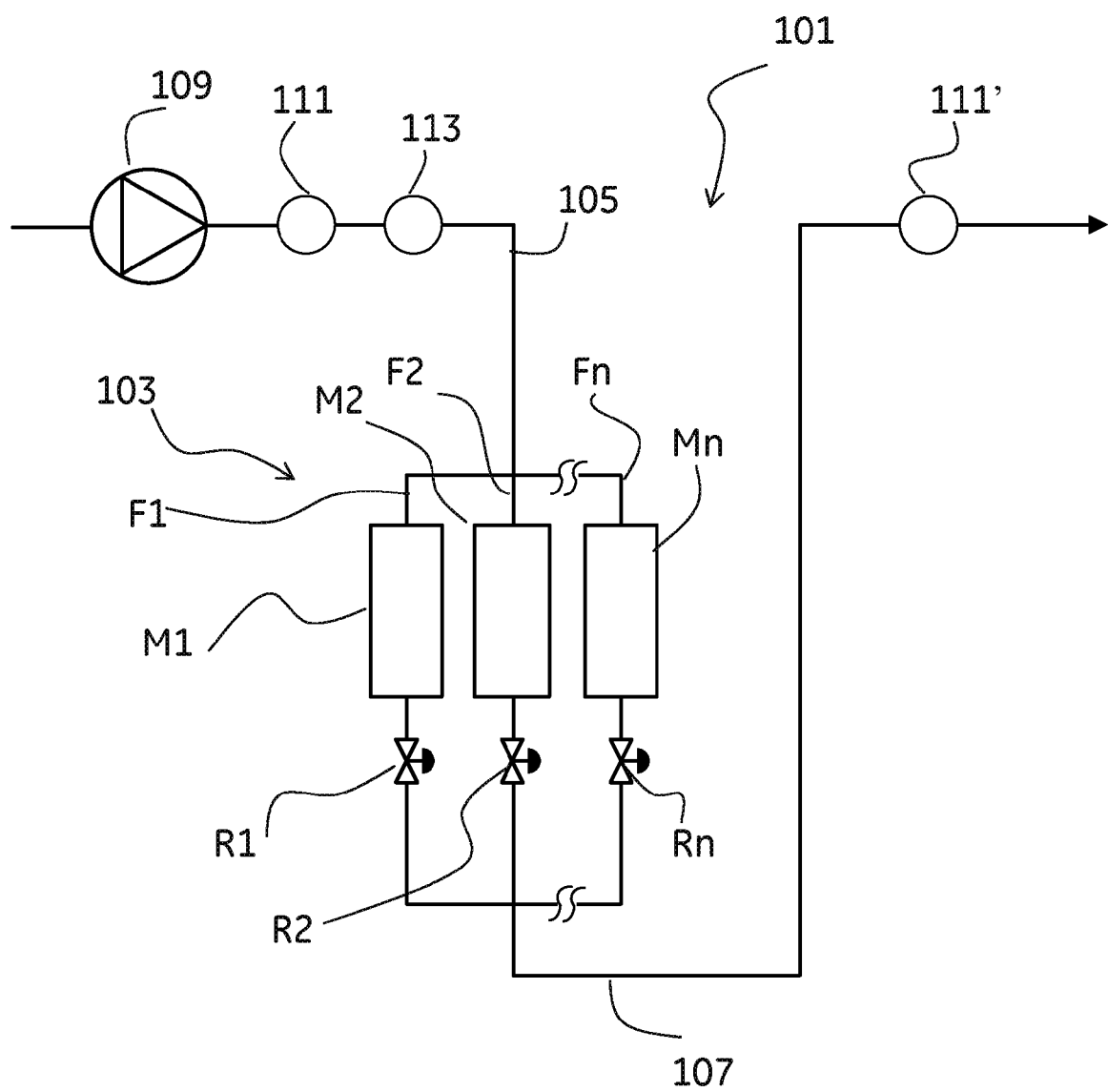
FIG. 9a is a flow scheme of a parallel assembly comprising adjustable flow restrictors according to one embodiment of the invention.

FIG. 9a is a flow scheme of a parallel assembly comprising adjustable flow restrictors according to this embodiment of the invention. FIG. 9a shows schematically a separation system 101 comprising a parallel assembly 103 of separation modules M1, M2, . . . Mn according to one embodiment of the invention. The parallel assembly 103 comprises a number of parallel fluid paths F1, F2, . . . Fn. Three fluid paths are shown here but it could be any number of parallel fluid paths. Each fluid path F1, F2, . . . Fn comprises a separation module M1, M2, . . . Mn. According to this embodiment of the invention each fluid path F1, F2, . . . Fn also comprises an adjustable flow restrictor R1, R2, . . . Rn. The adjustable flow restrictors R1, R2, . . . Rn should be possible to open completely, i.e. adjust to a position where no flow restriction is provided. Suitably the flow restrictors should also be possible to close completely, i.e. adjust such that no flow at all can pass. Alternatively or complementary a valve can be provided in each fluid path F1, F2, . . . Fn such that the fluid paths can be opened or closed. The separation system 101 further comprises an inlet fluid path 105 entering the parallel assembly 103 and an outlet fluid path 107 leaving the parallel assembly 103. The inlet fluid path 105 comprises in this embodiment a pump 109, a flow meter 111 and a pressure sensor 113. Alternatively the flow meter could be positioned downstream the parallel assembly 103, which is shown as flow meter 111'. In another alternative embodiment, the pump 109 in the separation system is a pump of metering type, hereby allowing for an a priori determination of delivered flow rate by calculation from a number of pump revolutions, a displaced volume or similar. In this alternative, flow meters 111 and 111' described above may be omitted as the flow rate is pre-determined. Yet another alternative embodiment of the system may employ a calibration curve for the system pump to avoid the need for a flow meter in the system.

The wetted part of the adjustable restrictors R1, R2, . . . Rn may be part of the corresponding separation modules itself and can therefore be disposable and of low cost. The controlling unit of the adjustable restrictors may be reusable, like a pinch valve principle, for example.

Figure 9B:
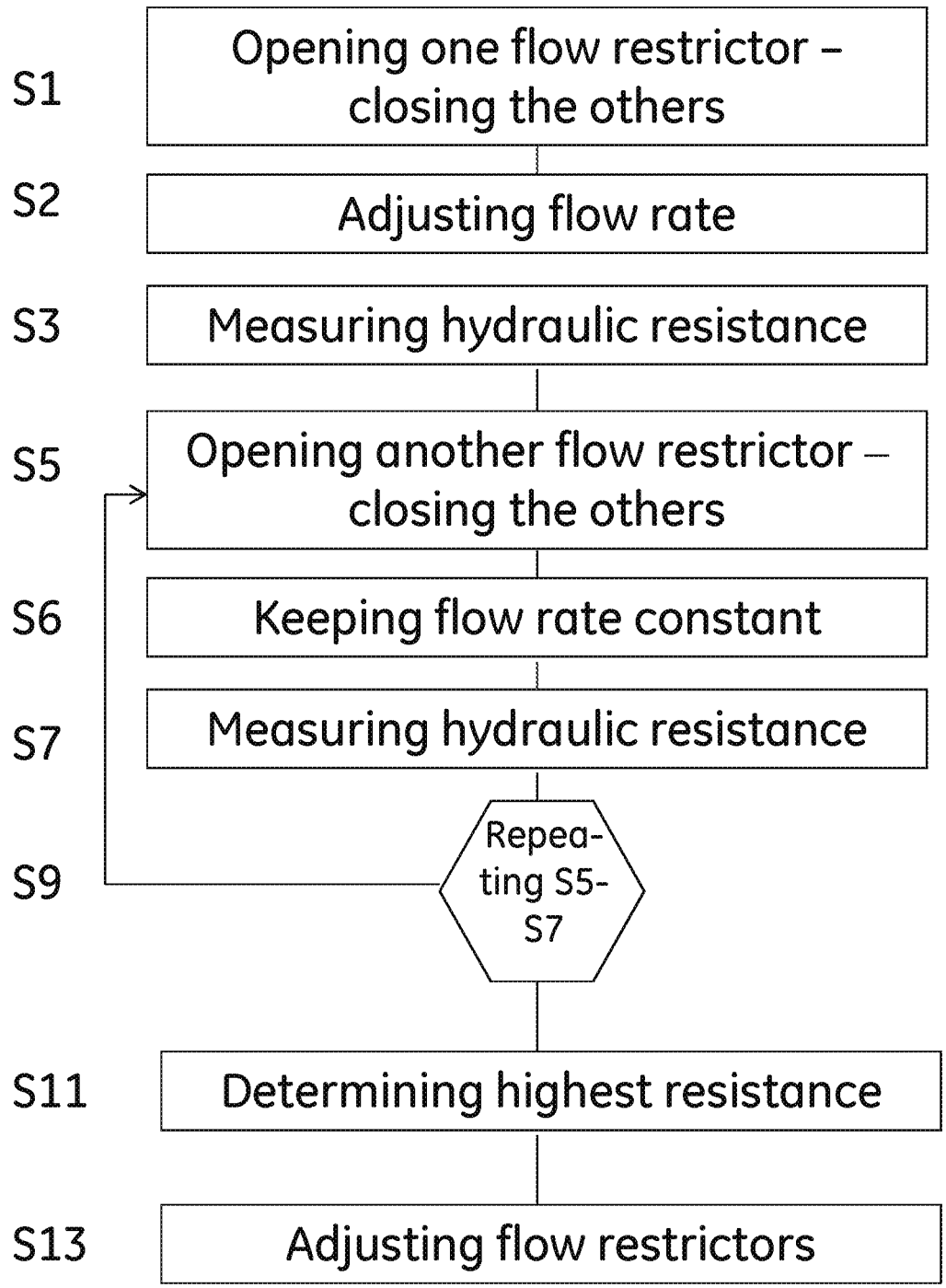

FIG. 9b is a flow chart of the method for adjusting hydraulic resistance in the flow paths. The method steps are described in order below.

S1: Opening one of the flow restrictors R1, R2, . . . Rn completely and at the same time closing all other flow restrictors completely, i.e. there will only be flow through one of the separation modules M1, M2, . . . Mn.

S2: Adjusting flow rate for hydraulic resistance measurement. Hydraulic resistance is measured by relating the measured pressure drop over the fluid line to the actual flow rate in this line, the latter may be measured by a flow meter or may be known in case of a metering pump or when using a calibration curve. In this example, the flow rate is adjusted to a defined constant flow rate. In practice, the flow rate will often be adjusted in proportion to the number of modules in the parallel assembly. For example, for a system set up with 5 modules that shall be operated in parallel with a system flow rate of 100 l/h over all modules, a flow rate of 100/5=20 l/h is suitably applied to the individual module when running the sequential identification of hydraulic resistance at each individual module and also when adjusting the hydraulic resistance subsequently. However, any constant flow rate could be applied as long as it allows for a predictable and scalable measurement and adjustment of the hydraulic resistance that ensures the synchronisation of the parallel assembly described by this invention. Given that this condition is followed, even different flow rates may be applied for measuring and adjusting the hydraulic resistance(s). Preferably, the flow rate selected in practice would be constant and within the range of typical operating flow rates suitable for the separation module and parallel assembly.

S3: Measuring the hydraulic resistance of the system, i.e. of the only fluid path that is open.

The hydraulic resistance is suitably measured by measuring a pressure loss over the open fluid path by a pressure sensor positioned upstream the parallel fluid path to be characterised. (pressure sensor 113 in FIG. 9a)

The hydraulic resistance of the system measured in S3 is substantially equal to the hydraulic resistance of the separation module in the fluid path where the flow restrictor has been completely opened.

S5: Opening another one of the flow restrictors R1, R2, . . . Rn completely and closing the others completely.

S6: Keeping the flow rate at the same constant level as in S2. If the pressure loss over the fluid path and separation module is in linear proportion to the flow rate over a wider range, the hydraulic resistance may be measured at different flow rates within said linear range. However, in practice the flow rate will be selected to the same constant level for measuring the resistance in all parallel lines.

S7: Measuring the hydraulic resistance of the system, i.e. the pressure loss over the fluid path comprising the flow restrictor that now is completely open. That is now the measure of the hydraulic resistance of the separation module comprised in that fluid path.

S9: Repeating the steps S5-S7 until all flow restrictors R1, R2, ... Rn has been completely opened and the hydraulic resistance of each one of the separation modules has been measured alone.

S11: Determining which one of the separation modules M1, M2, ... Mn having the highest hydraulic resistance. This is determined by comparing the measurement results from S3 and S7 above.

S13: Adjusting the adjustable flow restrictors R1, R2, ... Rn such that the hydraulic resistance of all the parallel fluid paths F1, F2, ... Fn is substantially the same as the hydraulic resistance of the separation module with highest hydraulic resistance. The goal is to achieve the same hydraulic resistance in all parallel fluid paths. Substantially the same is used here just to make it clear that it is hard to achieve exactly the same hydraulic resistance and also small differences should be covered by this invention. The differences should not be more than 10%, preferably less than 5%, and most preferable less than 2.5%. Hereby, the flow restrictor provided in the fluid path comprising the separation module having the highest hydraulic resistance need not be adjusted but kept open and all the other flow restrictors need to be adjusted such that the total hydraulic resistance in each fluid path, i.e. hydraulic resistance of separation module and flow restrictor, equals the hydraulic resistance of the separation module with highest hydraulic resistance. When performing the adjusting the flow rate is kept at the same constant level as in S2 and S6. Only the flow path comprising the flow restrictor to be adjusted is open and all other flow paths are closed and the pressure loss over the open flow path is watched by the pressure sensor. The adjustable restrictor of the open fluid path is adjusted until the measured pressure loss is equal to the pressure loss measured for the fluid path having the highest pressure loss (in other words hydraulic resistance) as measured in S3 and S5. By adjusting the hydraulic resistance in each flow path to match the characteristics of the flow path with the highest resistance as described above, the final pressure drop over the complete parallel assembly will be kept as low as possible, and required, respectively. Alternatively, it is of course possible to adjust the hydraulic resistance in each fluid path in the parallel assembly to match a hydraulic resistance that is higher than the measured highest hydraulic resistance in the fluid path of highest resistance. Hereby, the overall objective of synchronising the hydraulic resistance between all fluid paths will still be achieved, however, this will be on expense of higher overall pressure drop over the system at the operating flow rate.

An alternative to the procedure of measuring hydraulic resistance described above would be to measuring the hydraulic resistance of all fluid paths except one sequentially and additionally measuring the hydraulic resistance of the whole system and using these measurements (i.e. subtracting the hydraulic resistance of each separately measured fluid path from the hydraulic resistance for the whole system) for achieving the hydraulic resistance of also the last fluid path.

Figure 10:
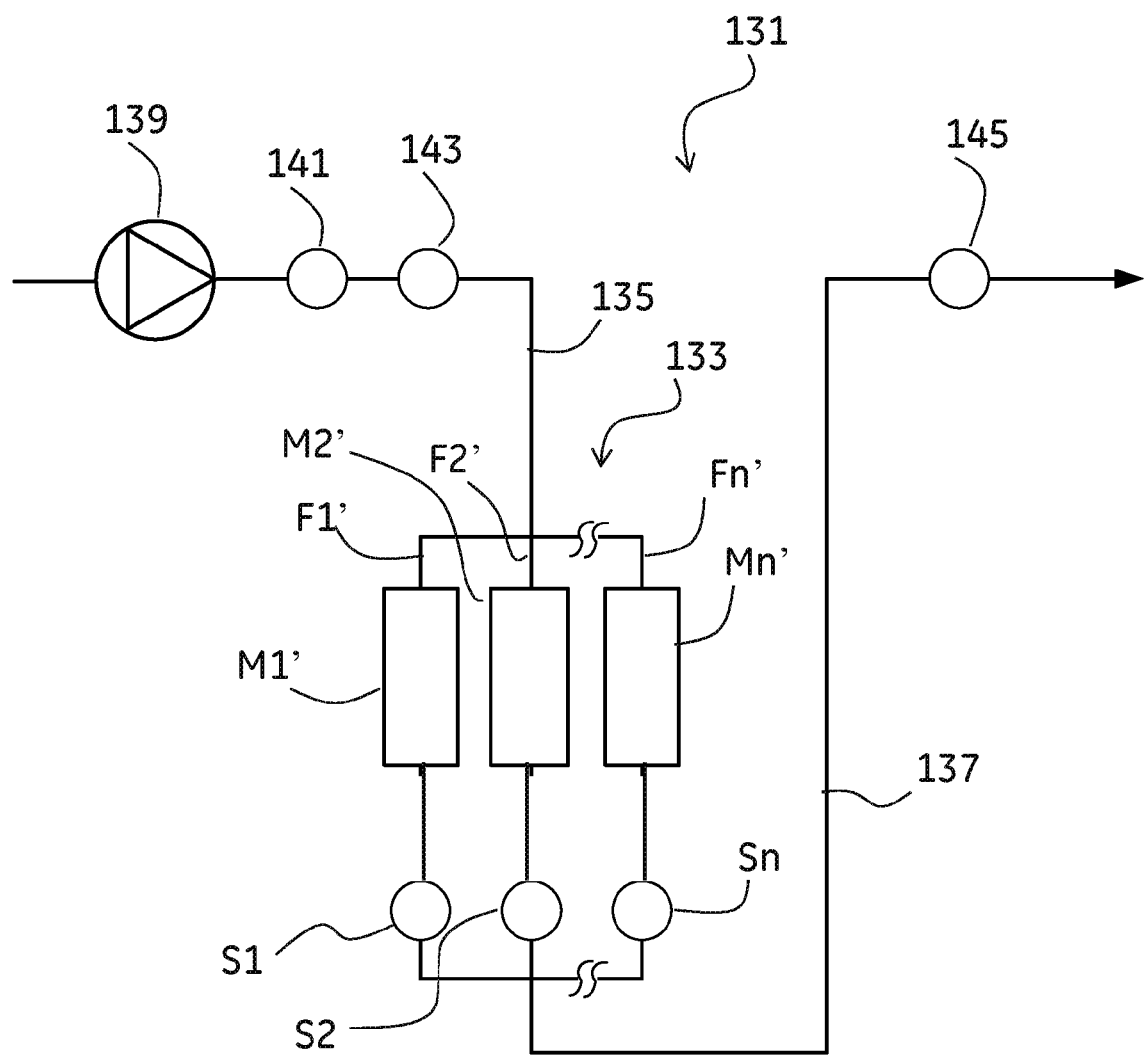
FIG. 10 is a flow scheme of a parallel assembly comprising sensors according to one embodiment of the invention.

FIG. 10 is a flow scheme of a parallel assembly comprising sensors according to one embodiment of the invention. FIG. 10 shows schematically a separation system 131 comprising a parallel assembly 133 of separation modules M1', M2', ... Mn' according to one embodiment of the invention. The parallel assembly 133 comprises a number of parallel fluid paths F1', F2', ... Fn'. Three fluid paths are shown here but it could be any number of parallel fluid paths. Each fluid path F1', F2', ... Fn' comprises a separation module M1', M2', ... Mn'. The separation system 131 further comprises an inlet fluid path 135 entering the parallel assembly 133 and an outlet fluid path 137 leaving the parallel assembly 133. The inlet fluid path 135 comprises in this embodiment a pump 139, a flow meter 141 and a pressure sensor 143. According to this embodiment of the invention each fluid path F1', F2', ... Fn' also comprises a sensor S1, S2, ... Sn and the outlet fluid path 137 in the system 131 comprises at least one system sensor 145. Sensors S1 ... Sn are adapted to measure the residence time and/or chromatographic efficiency over each individual separation module M1', M2', ... Mn' when running the separation modules in parallel and at the same time these features can also be measured on a system level by means of the system sensor 145. Hereby the overall response on system level as measured by the system sensor 145 can be compared to the individual response of each separation module as measured by the sensors S1 ... Sn. In an alternative embodiment of the invention sensors S1, ... Sn are only provided in all the fluid paths except one. The sensor response from the last fluid path can still be calculated by using the response from the system sensor and subtracting the other sensor responses. Suitably, these sensors are disposable probes measuring a characteristic fluid property, where the characteristic fluid property is of type fluid flow rate, example concentration, force, pressure, temperature, conductivity, pH or the absorbance, reflectance or emission of light as for example the measurement of UV absorbance.

The method steps using the sensors in the parallel assembly are:

a) Measuring a characteristic fluid property with said sensors (S1, S2, ... Sn) in the parallel fluid paths. Alternatively, measuring a characteristic fluid property with n−1 of said sensors, measuring the characteristic fluid property on system level and calculating the characteristic fluid property in the last fluid path.

b) Thereafter possibly measuring the same characteristic fluid property with the system sensor 145.

c) And finally comparing measured characteristic fluid properties to evaluate and/or qualify the performance of the separation system.

The evaluation of the separation system can be the measurement of residence time and/or chromatographic efficiency. The characteristic fluid property can be of type fluid flow rate, concentration, conductivity or changes in the absorption, reflection or extinction of light or energy. The comparison of sensor responses is done for the purpose of qualifying, monitoring or documenting the performance of the system.

The sensors can be integrated parts of the chromatography column modules. They can be disposable and they can possibly be connected to a re-usable counter part. For example a temperature measurement can be accomplished by providing a reusable IR sensor that is focused against a surface of the sing-le use column module, where said surface contains a process liquid and is at the temperature of the process fluid. A further example is a re-usable pressure sensor or load cell that is brought in contact with a flexible membrane confining the process fluid at side of the single-use module.

Figure 11:
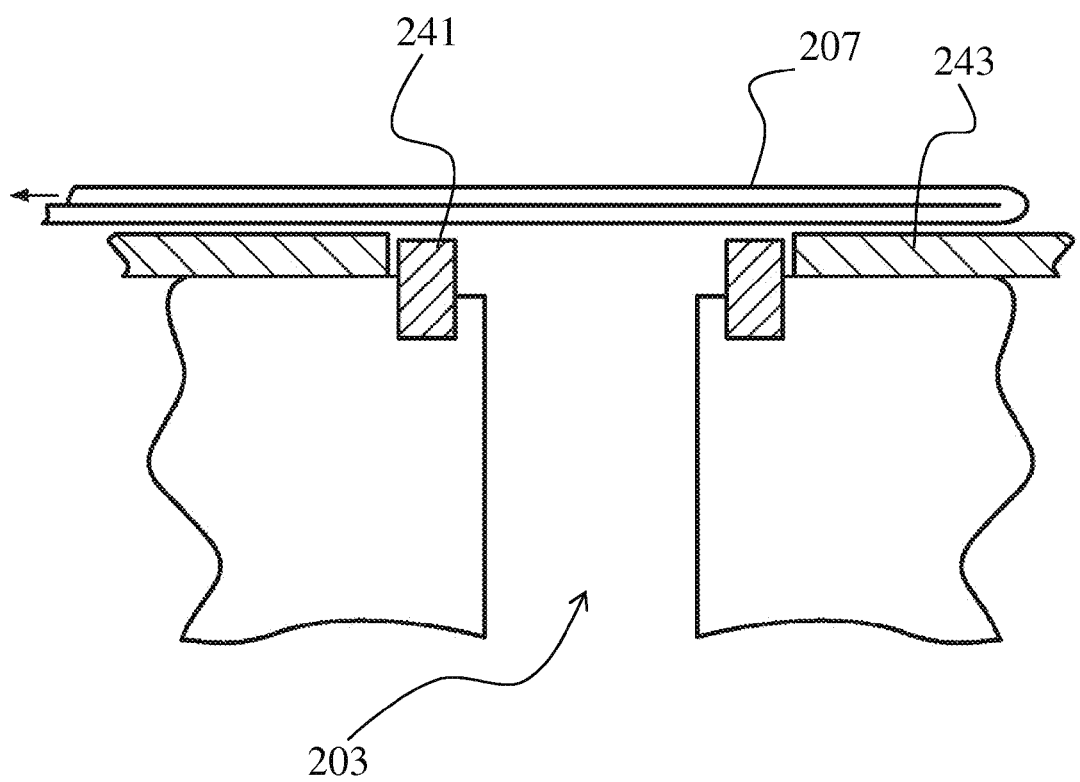
FIG. 11 shows schematically a folded film provided over a fluid connection for providing sterility.

FIG. 11 shows schematically a folded film 207 provided over a fluid connection 203 for providing sterility. With this embodiment of the invention any desired number of chromatography column modules can be connected to each other in a system in an aseptic way. Hereby an aseptic chromatography system, of any desired capacity can be built from units. Furthermore, these systems can be built in an environment that is not bioburden controlled and the system with all its connections will still be aseptic on process side. The word aseptic used in this description and in the claims shall have a broad definition, i.e. include any level of bioburden control. The bioburden control or asepsis can be measured as organisms/ml or CFU (colony forming units). In one embodiment of the invention the level of asepsis should be below 100 CFU/ml. The latter corresponds to bioburden control levels required for food grade products. Low levels of bioburden can be achieved by sterilisation processes. For example the modules of the invention can be subjected to gamma sterilization. Other possible methods are autoclaving or bioburden control by ethylene dioxide.

According to this embodiment of the invention a protection film 207 is provided over the fluid connections of the chromatography column modules. The film is suitably provided to the modules before the module is subjected to sterilisation. This means that the chromatography column modules with the attached film can be treated in a non sterile environment while the contents of the module confined by its inlets/outlets including the inlets/outlets still are kept sterile or aseptic. The film is folded over the fluid connections and one single sheet of the film is reaching outside the module. The film should be mated with a similar film on a connecting module and the two films should be released together by pulling the two single sheets reaching outside the modules when the modules are pressed together. This ensures that the fluid connections on the two modules will be connected in an aseptic way. Furthermore, to enable a fluid tight connection between the modules at least one gasket 241 is provided around each fluid connection or around a number of fluid connections if suitable for the device and application. A foam layer 243 is provided around the gaskets such that the modules can be pressed together to a first aseptic connection position where the protective films can be removed without exposing the aseptic process side to the environment, which may be non-sterile. The purpose of the compressible foam pads is to provide the required degree of volumetric variability to allow for an expansion of the two opposite foam pads against each other to remain asepsis when removing the adjacent folded films by pulling.

When the films have been released in this first connection position the modules are pressed together even further to a second position. In the second position a fluid tight seal is provided through the gaskets having been engaged.

Suitably the chromatography column modules are disposable, i.e. adapted to be used only once. Disposable or so-called single-use components are characterized that in that they are replaced (and disposed) in between different production processes, campaigns or even in between different process runs in order to reduce cleaning needs before, in between or after processing. The use of disposables allows not only for reduced downtime by elimination of cleaning steps and related quality control, it also increases product safety by eliminating problems with cross-contamination. A specific advantage with disposable systems is that there is no need for bioburden control and sterilisation before using the systems when using disposable systems that are already aseptic in some degree. Therefore the aseptic connection method and means provided with this embodiment of the invention is particularly interesting in disposable systems. With the invention disposable chromatography systems can be built up from different modules to a wanted capacity by the customer while still keeping the asepsis requirements.

In FIG. 11 a fluid connection 203 is shown. This fluid connection 203 could be any of the fluid connections provided on the column modules: 34a, b, c, d, 92a, b, the ends of the fluid conduits 83a, b, c, d, e, f, g, h, i, 85a, b, c, d, e, f, g, h, i or fluid connections 73a, b, c, d, e, f, g, h, i, 75a, b, c, d, e, f, g, h, i on a fluid distribution module 54a, 54b. Around the fluid connection 203 a gasket 241 is provided. One gasket can be provided around each fluid connection. In some cases it would also be possible to provide one gasket around more than one fluid connection. Furthermore a compressive foam layer 243 is provided around the gasket 241. The folded film 207 is provided over the fluid connection 203, the gasket 241 and the foam layer 243. The connection surface between the film 207 and the gasket 241 and the foam layer 243 is as described above aseptic.

The film 207 is folded unevenly such that the film is provided double over the fluid connection 203 and as a single sheet of the uppermost layer is reaching outside the chromatography column module. This part is used for being grabbed and for pulling out the film together with a matching film when the system is connected. When two chromatography column modules are connected the films are mated two and two together and during connection the films are supposed to be pulled out together two and two. Hereby the aseptic surfaces of the separation units (previously covered by the films) will be mated and the asepsis will be maintained.

Figure 12:
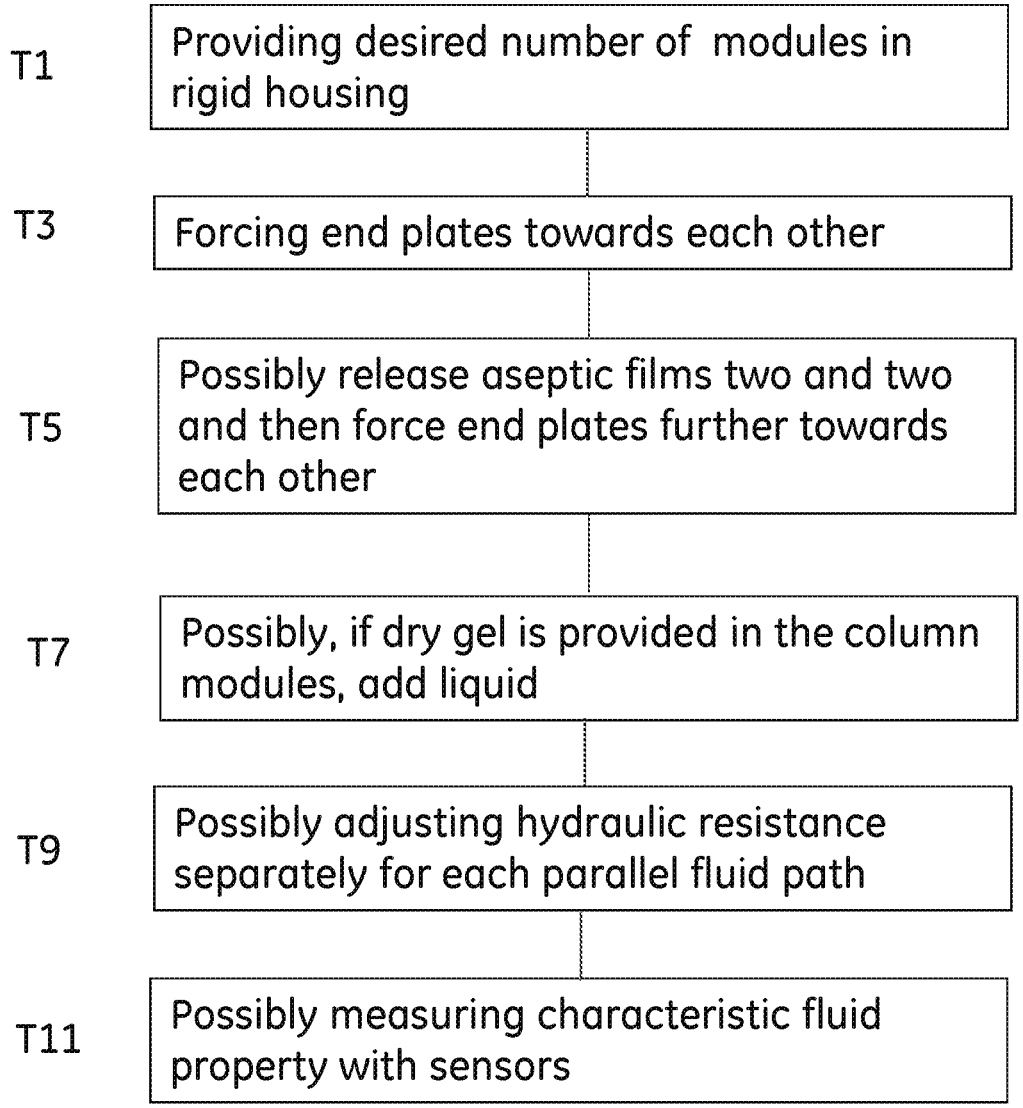
FIG. 12 is a flow chart of a method for connecting chromatography column modules in a rigid housing according to one embodiment of the invention.

FIG. 12 is a flow chart of a method for connecting column modules in a rigid housing according to one embodiment of the invention. The steps are described in order below:

T1: Providing a desired number of chromatography column modules in a stack in between end plates of a rigid housing. Fluid conduits of the column modules are facing each other.

T3: Forcing the end plates towards each other. Hereby fluid tight connections are achieved between the column modules.

T5: Possibly, if folded aseptic films 207 are provided to the fluid connections forcing the end plates towards each other to a first position for releasing the films two and two together and then forcing the end plates towards each other to a second position where fluid tight connection is achieved.

T7: Possibly, if dry gel is provided in the column modules, adding liquid to the column modules such that the dry gel will swell to take a volume that is a certain percentage larger than the bed space volume.

T9: Possibly, if adjustable restrictors are provided to the chromatography column modules, measuring the hydraulic resistance separately for each column module and adjusting the flow restrictors separately such that all the parallel fluid paths in the system have substantially the same hydraulic resistance.

T11: Possibly, if sensors are provided to the chromatography column modules, measuring a characteristic fluid property with at least one of said sensors in the parallel fluid paths and possibly measuring the same characteristic fluid property with a system sensor positioned in the outlet of the separation system and comparing measured characteristic fluid properties to evaluate and/or qualify the performance of the separation system.

The frame, i.e. the end plates, may be tilted 90 degrees for easy installation and in especially removal of the modules. The end plates may be clamped against each other by tie-bars or by an external clamping mechanism. Clamping elements (tie bars etc.) may be modular as well and built from short-length pieces to reduce overall size of the system and to increase flexibility and ease of use.

Figure 13A:
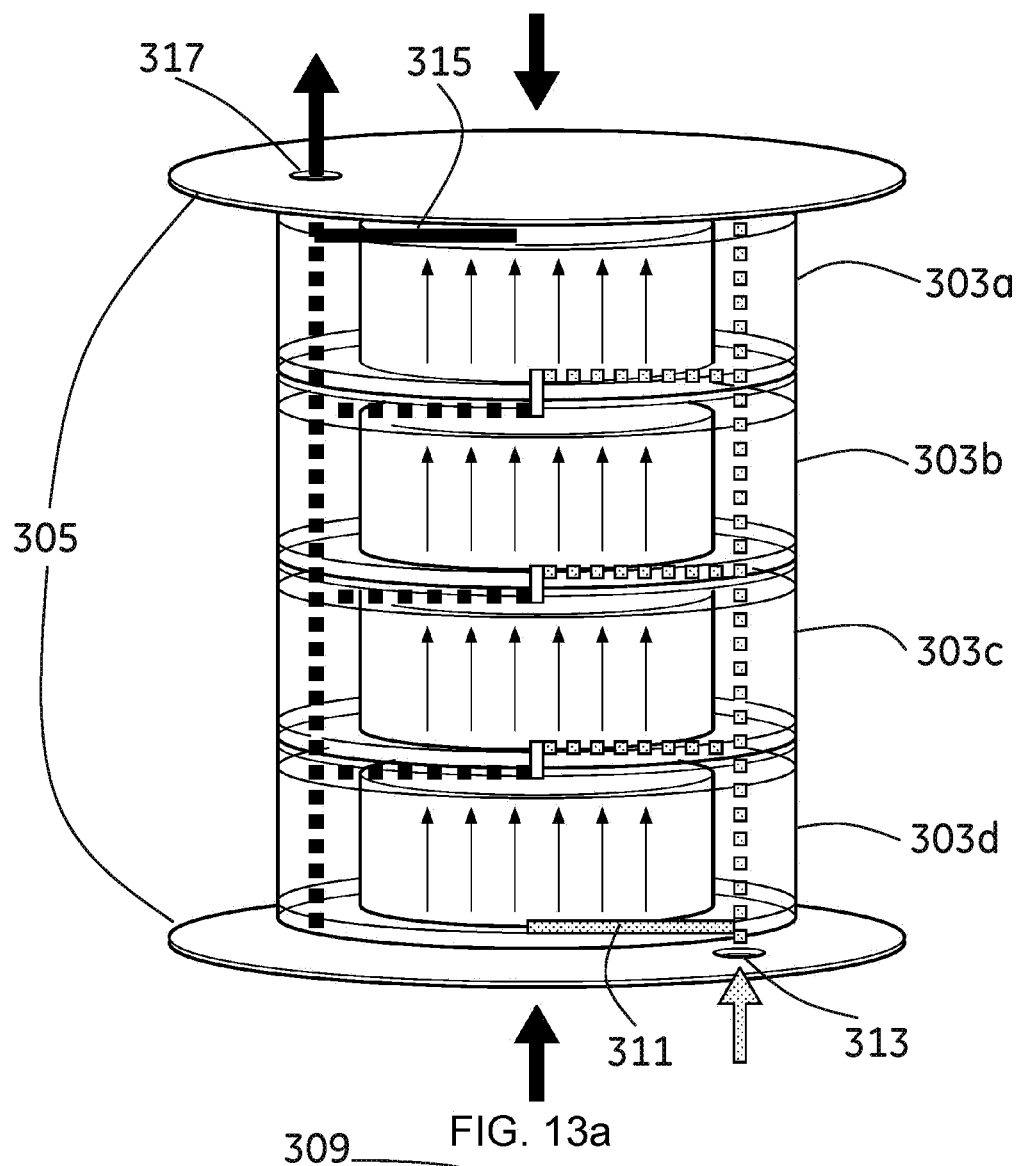
FIG. 13a shows schematically four chromatography column modules connected in series inside a rigid housing.

FIG. 13a shows schematically four chromatography column modules 303a, b, c, d connected in series inside a rigid housing 305. The number of serially connected chromatography column modules could of course vary.

Figure 13B:
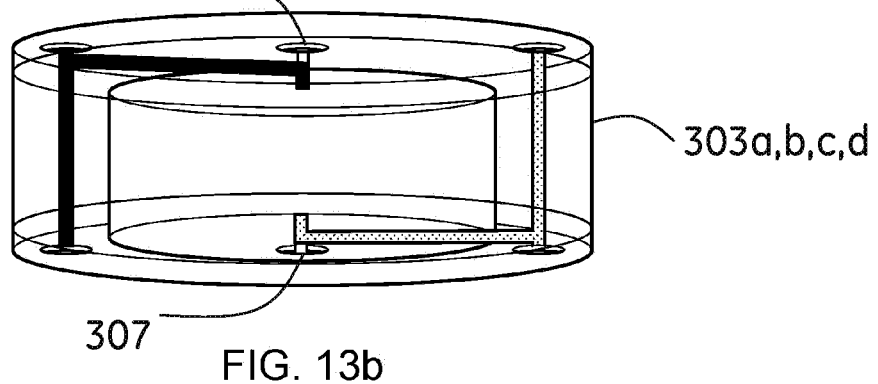

FIG. 13b shows schematically a chromatography column module 303a, b, c, d to be used in the system shown in FIG. 13a. For connecting the chromatography column modules in series a central inlet connection 307 and a central outlet connection 309 need to be provided for connecting inlet and outlet of possible chromatography column modules provided below or above the chromatography column module in question in the rigid housing. Fluid connections in the tubes of the chromatography column modules can suitably be shut off when the chromatography column modules are to be used in serial connections. This is shown in FIG. 13a with dotted lines. Besides the central inlet and outlet connections 307, 309 connecting adjacent chromatography column modules only one inlet fluid connection 311 connecting a common inlet 313 in the rigid housing with the central inlet connection 307 of the lowermost (referring to the orientation of FIG. 13a) chromatography column module 303d and one outlet fluid connection 315 connecting a common outlet 317 in the rigid housing with the central outlet connection 309 in the uppermost chromatography column module 303a are needed.

Furthermore these chromatography column modules 303a,b,c,d could be filled with dry chromatography medium as described above. The chromatography column modules are suitably disposable and they could also be provided with aseptic films over the fluid connections as described above. Furthermore sensors could be provided to the modules as described above.

The same base chromatography column module could suitably be provided both for chromatography column modules adapted to be connected in parallel and in series. By using any one of the different methods described above for configuring the end pieces of the chromatography column modules the fluid connections in the chromatography column modules can be adapted for either parallel or serial connection, i.e. one or more of the available fluid connections can be shut off for example by using insertions during or after moulding or removing of puncture webs as described above.

In all these embodiments described above the parts and surfaces being in contact with a process fluid are suitably selected from materials that are in accordance with typical material requirements in (bio-)pharmaceutical manufacturing or food grade quality. For example, materials are suitably in compliance with USP Class VI and 21 CFR 177. Furthermore they are suitably of animal-free origin and compliance to EMEA/410/01.

The chromatography column modules can in one embodiment of the invention be sterilized by gamma radiation.

The invention claimed is:

1. A parallel assembly of a stack of chromatography column modules connected in a rigid housing, the parallel assembly comprising:
    an assembly inlet;
    an assembly outlet;
    each chromatography column module comprising a bed space filled with chromatography medium and each chromatography column module comprises integrated fluid conduits which when the chromatography column module is connected with other chromatography column modules in the rigid housing the integrated fluid conduits are connected to the bed space of the chromatography column module with the assembly inlet and the assembly outlet;
    each integrated fluid conduits comprise a total length and a volume, wherein at least one of the total length and the volume of the fluid conduit from the assembly inlet to one bed space together with at least one of the total length and the volume of the fluid conduit from the same bed space to the assembly outlet is substantially the same (less than 20%) for all bed spaces and modules installed in the parallel assembly; and
    further comprising two fluid distribution modules arranged at each side of the stack of column modules, each fluid distribution module have one distribution module fluid connection representing the assembly inlet or assembly outlet of the parallel assembly and a connection face towards the stack of column modules, the connection face having at least two connection face fluid connections for connecting to the inlet or outlet side of at least two stacked chromatography column modules.

2. The assembly of claim 1, wherein the rigid housing having a first end plate and a second end plate, wherein the assembly inlet is configured to pass through the first end plate and the assembly outlet is configured to pass through the second end plate.

3. The assembly of claim 2, wherein the first end plate applies a first directional force to a first column module of the plurality and the second end plate applies a second directional force to a final chromatography column module of the assembly thereby securing the fluid conduits of the each chromatography column module to the preceding and succeeding chromatography column modules.

4. The assembly of claim 1, further comprising a connection face positioned adjacent the assembly of chromatography column modules, the connection face having at least two connection face fluid connections for connecting to the fluid conduits of at least two column modules.

5. The assembly of claim 1, wherein the parallel assembly of chromatography column modules has at least two serially connected chromatography column modules.

6. The assembly of claim 1, wherein one or more of the chromatography column modules is disposable.

7. The assembly of claim 1, wherein the fluid conduits are manufactured with integrated fluid conduits.

8. The assembly of claim 1, wherein an inlet fluid conduit comprises a first seal preventing movement of the first volume prior to attachment of the preceding column module and an outlet fluid conduit comprises a second seal preventing movement of the second volume prior to attachment of the succeeding column.

9. The assembly of claim 1, wherein the bed space is prefilled with dry chromatography gel in an amount such that when liquid is added to the bed space the dry gel will swell to a volume occupied in a non confined space that is at least 2% larger than the volume of the confined bed space.

10. The assembly of claim 1, wherein the each chromatography column module comprises a sensor.

11. The assembly of claim 1, wherein the each chromatography column module comprises an adjustable flow restrictor.

12. The assembly of claim 1, wherein aseptic films are provided to fluid connections between each of the chromatography column modules and between the chromatography column modules and the rigid housing.

* * * * *